United States Patent [19]

Strupat

[11] 4,232,668
[45] Nov. 11, 1980

[54] GAS VENTILATING DEVICE

[76] Inventor: John P. Strupat, #127-1560 Adelaide St., N., London, Ontario, Canada, N5X 2C1

[21] Appl. No.: 15,886

[22] Filed: Feb. 28, 1979

[51] Int. Cl.³ ............................................. A61M 16/00
[52] U.S. Cl. ................................................. 128/204.24
[58] Field of Search ............... 128/145.8, 145.5, 145.6, 128/142.2, 204.21, 204.24, 204.25, 204.27, 205.24; 137/826, 835, 820, 821, 624.14

[56] References Cited

U.S. PATENT DOCUMENTS

| | | | |
|---|---|---|---|
| 2,760,511 | 8/1956 | Greeff | 137/102 |
| 3,831,596 | 8/1974 | Cavallo | 128/145.8 |
| 3,902,487 | 9/1975 | Okmian | 128/145.8 |
| 4,120,300 | 10/1978 | Tiep | 128/145.8 X |

Primary Examiner—Henry J. Recla
Attorney, Agent, or Firm—Mitches & Co.

[57] ABSTRACT

The invention discloses a gas ventilating device where the tidal volume during the inhalation phase of any cycle of patient consumption is constant and fixed; hence, the deliverable volume is independent of the head pressure of the supply source of the gas. Further, the tidal volume can be controlled by altering the differential pressure of the gas in a fixed volume tank which acts as an intermediate storage tank for gas. Control means, using fluidic devices including monostable and bistable devices control the charging and discharging of the fixed volume tank with gas so that the fixed volume of gas can be supplied to the patient.

7 Claims, 7 Drawing Figures

GAS VENTILATING DEVICE

This invention relates to a gas ventilating device and particularly for a device to ventilate patients.

In the prior art various ventilating devices and resuscitators exist. For the purposes of this disclosure, "ventilators" shall be deemed to include devices which force air into the lungs of a patient whereby on flow termination the chest cavity relaxes and the patient thereby exhales. "Resuscitators" shall include a device which, contrary to a ventilator, supplies air flow to the lungs of a patient who mobilizes his own chest cavity to expand the same thus reducing the air pressure therein relative to the source of supply. This causes, a flow of air into the lungs.

Two interesting prior art ventilators and resuscitators will be discussed. In one, a control means regulates the cycle time of each phase of flow (ventilation) of gas to the patient and non flow (expiration) of gas from the patient. The relative duration of each phase and the flow rate is controlled. The volume of gas supplied to the patient is only indirectly regulated since it is dependent upon the head pressure of the supply source and the duration of the ventilation phase. This type of system is disclosed by Springer in his U.S.A. Pat. No. 3,522,818 issued Aug. 4, 1970 for a "Fluid System for Filling and Emptying an Enclosure". It has met with limited commercial success because in Operating Theatre applications the volume of air passed to a patient during resuscitation or ventilation conditions is critical in the control of the body metabolism and vital signs.

On the other hand, it is known that a resuscitator may be constructed to give a given volume of gas during an extended duration of each inhalation phase of the patient. This is achieved by prior charging a tank of predetermined volumetric size to a predetermined pressure; then venting the tank through an appropriate delivery means such as a face mask to a patient. The volume delivered is thus known if the tank pressure always drop to a known pressure. This may be assured by making the gas delivery phase of the cycle of extended duration so that the tank pressure is assured to drop to the predetermined known pressure. Such devices however are also arranged to also provide cardiac compression during the opposite phase of each cycle while maintaining the duration of cycle and of each phase thereof relatively fixed and unvariable.

I have discovered that a ventilator, which is more desirable than a resuscitator for Operating Theatre applications, may be constructed so as to deliver given and determinable volumes of gas to a patient. This is achieved in in a manner which is independent of duration of patient ventilation (inhalation). This feature avoids any deviation in the volume of air delivered to a patient during each ventilation phase. (Volume deviation is a common complaint of prior art devices and is usually caused by increased resistance within the delivery supply means to the patient). It also has the characteristic of controlling the duration of the ventilation phase only so long as to accomplish delivery of the given volume of gase.

Thus, my embodiment does not tend to reduce the volume of gas flow to a patient because of delivery supply resistance over the delivery period since cycling is dependent on the delivered volume, not the time duration, of air flow to the patient.

The tidal volume therefore delivered to a patient according to my embodiments during the ventilation phase may be simply controllable as by controlling the differential in the pressure of a tank of fixed volume at the beginning and the termination of the ventilation phase; hence, the deliverable volume is independent of the head pressure of the supply source of the gas. Further, in my preferred embodiment the differential pressure in the tank can be easily adjusted whereby the tidal volume of gas delivered to the patient is minutely controlled. The control means is preferably by fluidic devices although in alternative embodiments a mixture of fluidic and electro-mechanical equivalents thereof may be used.

In yet another variation of the embodiments the ventilator will respond to patient demands and terminate the patient expiration phase in each cycle and initiate the ventilation phase.

In order to accomplish the above an apparatus is provided for filling an enclosure with fluid of given volume in cycles including:
(a) a first phase for delivery of fluid to the enclosure until the pressure therein reaches a predetermined high pressure point; and,
(b) a second phase for ventilating the fluid in the enclosure to a patient until the pressure in the enclosure reaches a predetermined low pressure point.

More specifically the invention contemplates an apparatus for ventilating a patient with a given volume of fluid comprising:
(a) a source of fluid under pressure;
(b) a tank of fixed volume;
(c) delivery means for delivering fluid to the patient;
(d) first passage means extending from the source to said tank in a normally open state;
(e) second passage means extending from said tank to said delivery means in a normally closed state;
(f) sense and switch means for sensing a high point and a low point in the pressure in the tank and at each point reversing the states of the first and second passage means whereby, in the first state fluid flows from the source into the tank and in the second state from the tank through the delivery means to the patient.

The invention will now be described by way of example and reference to the accompanying drawings in which.

Figure 1:
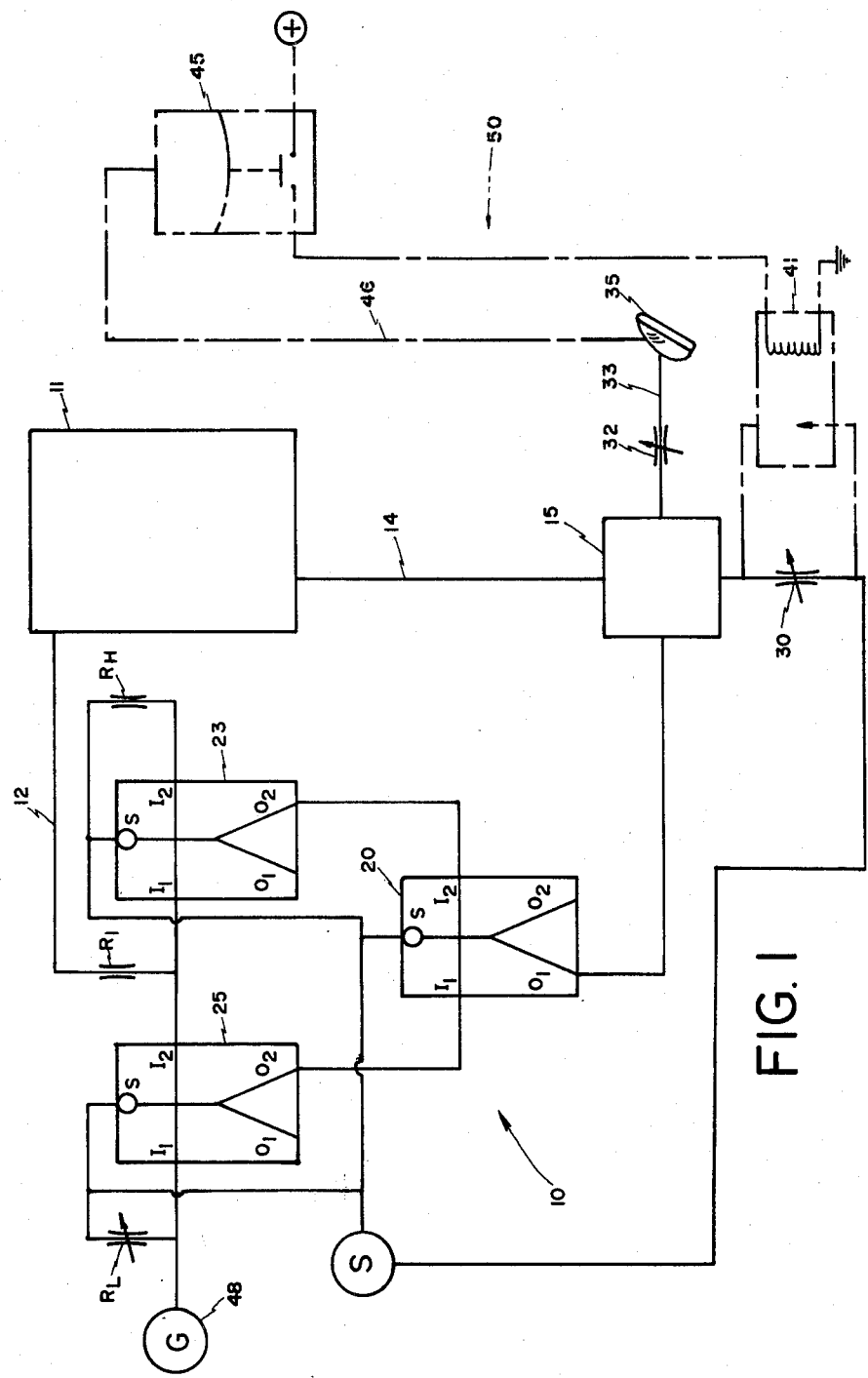
FIG. 1 is the schematic diagram of the preferred embodiment employing fluidic devices.

Referring now to FIG. 1 a source S of fluid supply, for example oxygen, a tank 11 of fixed volumetric size and a fluid flow switch 15 compose the major principal operative elements of my novel apparatus. The fixed volumetric tank 11 has a sensing channel 12 which communicates through a pressure valve R1 to the input ports 25-I2 and 23-I1 of two monostable fluidic operative devices 25 and 23. Each of the input ports of a third bistable fluidic operative device 20 (I1 and I2) are respectively connected to one output port of the two monostable devices 23 and 25 (namely the 02 output ports). The tank 11 has an input feed or channel 14, which in one phase also acts in part as a output channel, connected to flow switch 15. The flow switch 15 periodically connects on the one hand the supply source S to the tank 11 and on the other hand tank 11 to a face mask 35 for communication of fluid to the patient for ventilation. The face mask 35, a variable pressure valve 32 and a conduit 33 and the common portion of conduit 14 act as the delivery means of fluid gas from the tank 11 to the patient. The switch valve 15 is normally in the gas delivery phase and communicates the fluid source S to the conduit 14 so that the tank 11 is filled. On receiving a pulse from output part 20-01 the valve disconnects the source from the conduit 14 and gas flows from the tank 11 through conduits 14 and 33 to the patient mask 35 for ventilation of the patient hence the ventilation phase. The input ports of the monostable device 25 are respectively connected, 25-I1 to the source S and 25-I2 to one of the input ports of the other monostable device 23 (23-I1). The other input port of device 23 (23-I2) loops to the source of that device through a high point pressure reference valve RH while in much the same manner the source port of device 25 communicates to the input port (25-I1) through a low point reference pressure valve RL, which is preferably variable. A pressure gauge 48 indicates this lower reference pressure.

Figure 2:
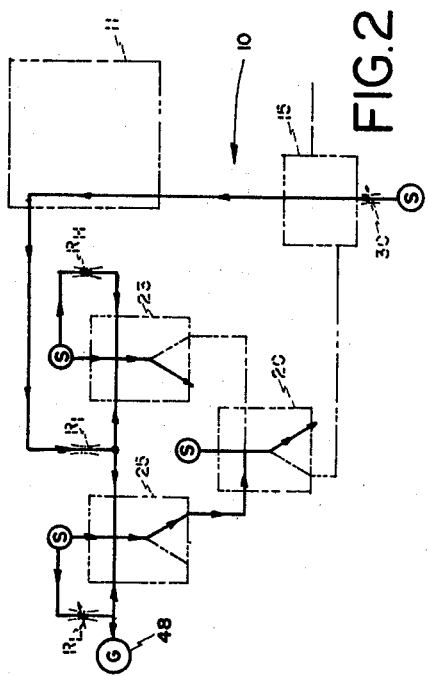

Now referring to the operation of the apparatus 10 FIG. 2 represents the fluid flow when the source S is first attached or first connected to the apparatus 10. Gas flows from the source S into the supply port S of device 25 and to input 25-I1 through the low pressure reference valve RL. Flow continues through the device 25 out port 25-02 and into the input port 20-I1. In the meantime the flow also is initiated from the source S through valve 15 and conduit 14 into the tank 11. The sensing feed 12 communicates the ambient pressure in the tank 11 to input ports 23-I1 and 25-I2.

Figure 3:
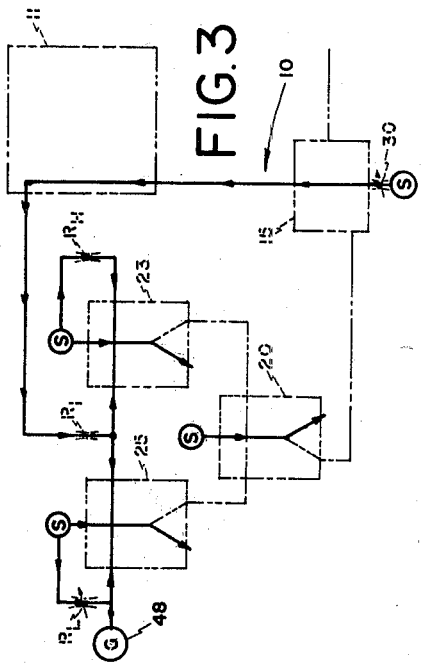

As soon as the pressure within the tank reaches the low reference pressure established by valve RL the flow pattern switches to that of FIG. 3 as at this instant, pressure at 25-I2 is higher than that at 25-I1 and the flow is switched to output port 25-01. This does not change the output for the bistable device 20.

Figure 4:
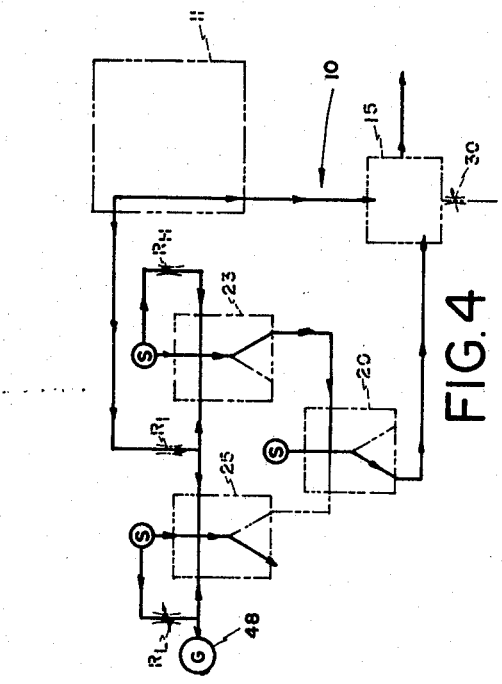
FIGS. 2 through 5 are explanatory flow diagrams of the embodiment of FIG. 1 showing the fluid flows during various critical boundary conditions of operation.

Referring to FIG. 4., when the pressure in the tank 11 exceeds the high pressure reference RH communicating with monostable device 23 the output is switched to output port 23-02 since the pressure at the input port 23-I1 is higher than at 23-I2. This causes the bistable device 20 to shift its output to 20-01 which in turn causes the switch 15 to terminate the gas flow from the source S into the tank 11 and to connect the tank to the mask 35. Patient ventilation beings. The tank 11 begins to empty.

Figure 5:
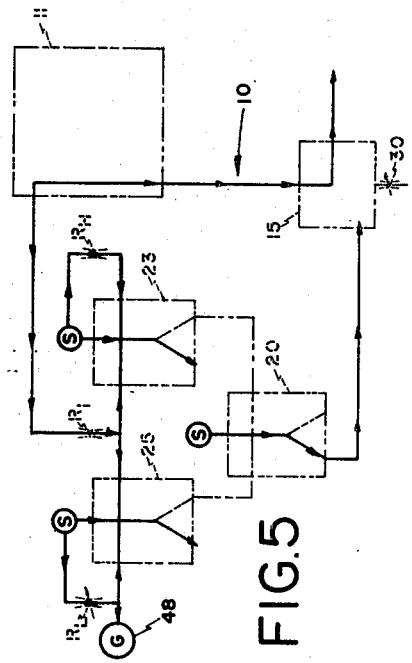

Referring to FIG. 5, the pressure in the tank 11 is decreasing as gas flows to the mask 35. When this pressure is incrementally less than the high pressure reference RH the pressure at input port 23-I2 is greater than that at 23-I1 thereupon the fluid supply is switched to 23-01. This does not change the output state for bistable device 20 so the pressure in the tank 11 continues to decrease (and flow to the face mask 35 is maintained) until the low pressure reference point RL is reached, whereupon, the flow pattern of FIG. 2 is resumed when the pressure in the tank 11 is incrementally less then the lower reference pressure RL. When the pressure at input 25-I1 is greater than at 25-I2 and the fluid supply is switched to 25-02, this changes the output of bistable element 20 to 20-02; the valve 15 now reconnects the source S to the tank 11. The tank 11 is charged again and the patient exhalation phase is initiated.

By regulating the low pressure reference point with the aid of a variable low pressure regulator RL the low pressure point of the tank 11 may be shifted and hence the differential in pressure between the high pressure point and low pressure point within the tank altered. Since the tank is of fixed volume the tidal volume of gas delivered by the tank during ventilation (delivery phase of FIG. 4) is varied.

There may be included a patient demand system shown in phantom as 50 in FIG. 1. The patient demand system consists of a normally closed electro-pneumatic valve 41 in parallel with, or across, a variable pressure valve 30 and a differential pressure valve 45 connected to the patient mask 35 via conduit 46. The patient demand during exhalation of the patient produces current flow through differential pressure valve 45 to activate the electro-pneumatic valve 41 and thereby allow an unrestricted gas flow from source S to tank 11. This instantaneously ends the exhalation period immediately by quickly filling the tank 11 to the high reference pressure. Ventilation thus is initiated as above explained.

Figure 6:
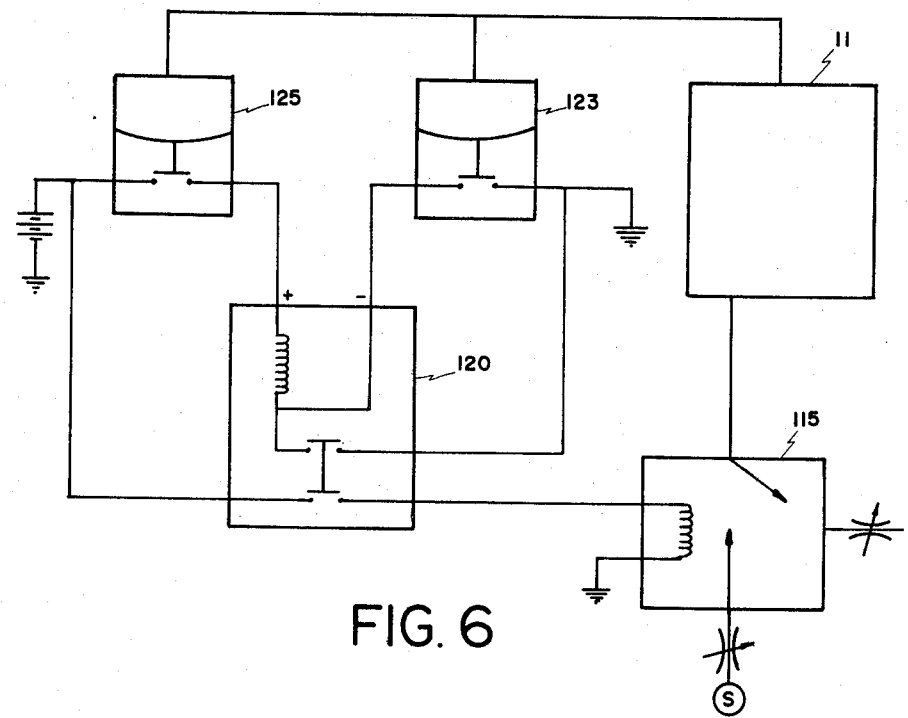
FIG. 6 is schematic diagram of an alternative embodiment employing electro-mechanical devices and fluid devices.

Referring to FIG. 6 fluidic monostable devices 25 and 23 are respectively replaced with differential pressure valves 125 and 123 while the bistable device 20 is replaced by an electrically operated switch 120. Switch 15 is replaced with a double throw single pole electro-pneumatic switch 115. They operate similar to that of FIG. 1.

Figure 7:
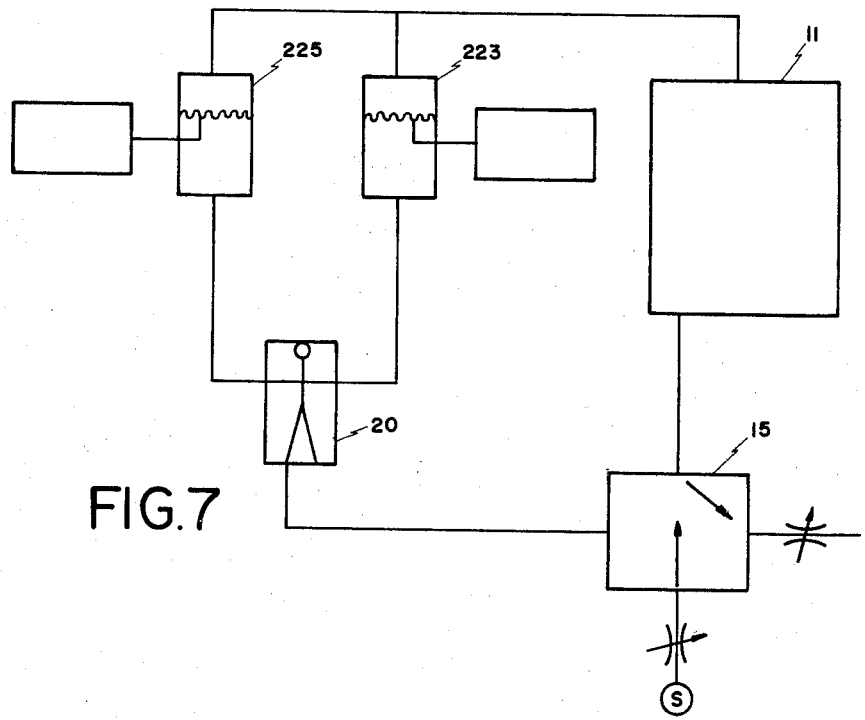
FIG. 7 is a further alternative embodiment.

Yet another embodiment, FIG. 7, shows differential pressure valves 225 and 223 replacing the fluidic switches 25 and 23 while leaving the fluidic switch 20 intact.

Those skilled in the art will now appreciate that the various components of the apparatus may be altered while maintaining the embodiments of the invention.

In the embodiments of the invention in which an exclusive property or privilege is claimed are defined as follows:

1. An apparatus for filling a fixed hollow enclosure with fluid of given volume and for evacuating the same to deliver a fixed volume of gas in successive cycles including:
 (a) means for delivery of a first phase of fluid to the enclosure until the pressure therein reaches a predetermined high pressure point; and,
 (b) means for delivery as a second phase a fixed volume of the fluid in the enclosure to a patient until the pressure in the enclosure reaches a predetermined low pressure point; including conveying means for conveying the fluid from the enclosure to the patient.

2. The apparatus as claimed in claim 1 including means for delivery of an initial volume of fluid to the enclosure until the low pressure point is reached so that the first phase means may be initiated.

3. An apparatus for ventilating a patient with a given volume of fluid comprising:
 (a) a source of fluid under pressure;
 (b) a tank of fixed volume;
 (c) delivery means for delivering a fixed volume of fluid at a predetermined pressure to the patient;
 (d) first passage means extending from the source to said tank in a normally open state;
 (e) second passage means extending from said tank to said delivery means in a normally closed state;

(f) sense and switch means for sensing a high point and a low point in the pressure in the tank and at each point reversing the states of the first and second passage means whereby, in the first state fluid flows from the source into the tank and in the second state from the tank through the delivery means to the patient.

4. The apparatus as claimed in claim 3 wherein the parts of the first and second passage means are a common passage.

5. The apparatus as claimed in claim 3 additionally comprising a pressure sensing conduit communicating with the tank and to 1st and 2nd pressure responses switch means, said first pressure response switch means generating the signal when the pressure in the tank is above a high pressure reference point, said second pressure response switch means generating a signal when the pressure in the tank is below the low pressure reference point, each signal communicating to a bi-stable switch responsive to generate and to reverse its output on receipt of one of said signals whereupon the state of the output of the bistable switch determines the normally open state or closed state of both passage means.

6. The apparatus as claimed in claim 5 wherein the first and second pressure responses switch means are fluidic devices.

7. The apparatus as claimed in claim 5 or 6 wherein the bi-stable switch is a fluidic device.

* * * * *